(12) United States Patent
Foley

(10) Patent No.: US 7,519,433 B2
(45) Date of Patent: Apr. 14, 2009

(54) GASTROINTESTINAL STIMULATION LEAD

(75) Inventor: Stephen T. Foley, Kerrville, TX (US)

(73) Assignee: Medtronic Transneuronix, Inc., Minneapolis, MN (US)

( * ) Notice: Subject to any disclaimer, the term of this patent is extended or adjusted under 35 U.S.C. 154(b) by 45 days.

(21) Appl. No.: 10/926,160

(22) Filed: Aug. 25, 2004

(65) Prior Publication Data

US 2006/0047323 A1 Mar. 2, 2006

(51) Int. Cl.
*A61N 1/05* (2006.01)
*A61B 5/04* (2006.01)

(52) U.S. Cl. .................. 607/133; 607/126; 600/386

(58) Field of Classification Search ............ 607/115–6, 607/121, 122, 124, 133, 126–8; 600/373–5, 600/377, 380, 386
See application file for complete search history.

(56) References Cited

U.S. PATENT DOCUMENTS

| | | | |
|---|---|---|---|
| 5,423,872 A | 6/1995 | Cigaina | |
| 5,439,485 A * | 8/1995 | Mar et al. ................... | 607/119 |
| 5,690,691 A | 11/1997 | Chen et al. | |
| 5,836,994 A | 11/1998 | Bourgeois | |
| 5,861,014 A | 1/1999 | Familoni | |
| 6,041,258 A | 3/2000 | Cigaina et al. | |
| 6,321,124 B1 | 11/2001 | Cigaina | |
| 6,510,332 B1 * | 1/2003 | Greenstein ................. | 600/377 |
| 6,606,523 B1 | 8/2003 | Jenkins | |
| 6,615,084 B1 | 9/2003 | Cigaina | |
| 7,016,735 B2 * | 3/2006 | Imran et al. .................... | 607/40 |
| 2003/0045919 A1 * | 3/2003 | Swoyer et al. .............. | 607/122 |
| 2003/0195600 A1 * | 10/2003 | Tronnes et al. .............. | 607/116 |
| 2004/0088022 A1 | 5/2004 | Chen | |

FOREIGN PATENT DOCUMENTS

| | | |
|---|---|---|
| WO | WO 98/53878 | 12/1998 |
| WO | WO 00/61223 | 10/2000 |
| WO | WO 00/61224 | 10/2000 |

OTHER PUBLICATIONS

Notification of Transmittal of the International Search Report and the Written Opinion for PCT Application No. PCT/US2005/028616, dated Sep. 15, 2006 (9 pgs).
International Preliminary Report on Patentability for PCT Application No. PCT/US2005/028616, dated Feb. 28, 2007 (6 pgs.).

* cited by examiner

*Primary Examiner*—Carl H Layno
*Assistant Examiner*—Natasha N Patel
(74) *Attorney, Agent, or Firm*—Schumaker & Sieffert, P.A.

(57) ABSTRACT

An implantable lead device and method for implanting the lead, wherein the lead device electrically stimulates tissue within a patient's body and more particularly the lead device stimulates gastrointestinal tissue. The implantable lead may be inserted through the tissue with minimal expansion of the penetration tunnel and attached to the tissue being stimulated with minimal efforts or apparatus. The implantable lead has flexible properties thus minimizing the potential for electrode erosion, maximizing tissue compliance, and minimizing the mechanical stress concentration that may result in fatigue failure in the lead.

73 Claims, 4 Drawing Sheets

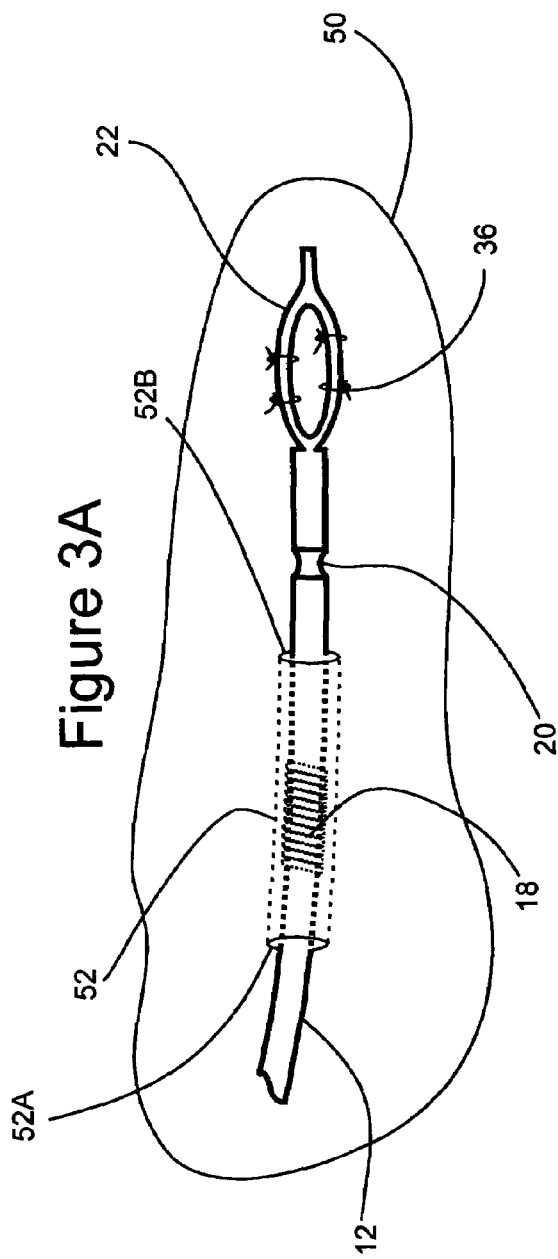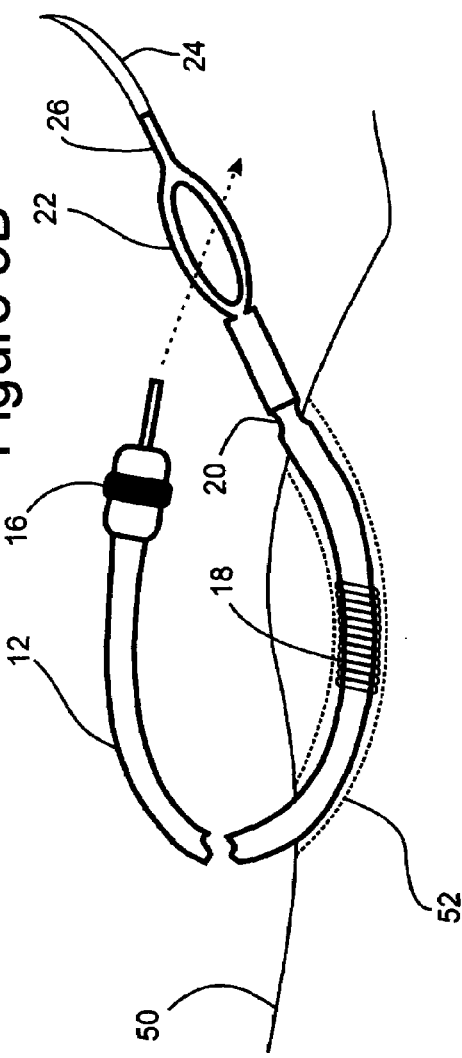

GASTROINTESTINAL STIMULATION LEAD

FIELD OF THE INVENTION

The present invention relates to implantable lead devices and methods for implanting such lead devices, wherein the lead device electrically stimulates tissue within a patient's body (especially gastrointestinal tissue). More particularly, the implantable leads may be inserted through the gastrointestinal tissue with minimal expansion of the tissue tunnel and affixed to the gastrointestinal tissue with minimal efforts or apparatus. The implantable lead has flexible properties thus minimizing the potential for electrode erosion, maximizing tissue compliance, and minimizing the mechanical stress concentration that may result in fatigue failure in the lead.

BACKGROUND OF THE INVENTION

It is well known that more than 70% of illnesses affecting the digestive tract are of a functional nature. Today such illnesses are treated predominantly using pharmacological means. Since drugs generally have side effects, particularly when the drugs only address the symptom and not the underlying problem or dysfunction, they must often be administered for only relatively short period of time. Indeed, if the side effects are sufficiently serious, the drug may have to be discontinued before full benefit to the patient is realized; in many cases the underlying illness remains.

The important role played by electrophysiology in controlling gastrointestinal activity has become increasingly apparent in recent years. Thus, the possibility exists of correcting dysfunction by means of electrical stimulation applied at specific frequencies, sites, and modalities and with regard to the self-regulating electromotor physiology of the gastrointestinal organs or tract. It has recently been shown, for example, that changes occur in the motility and electromotor conduct of the gastric tract in eating disorders (e.g., obesity, thinness, bulimia, anorexia). Disturbances in electromotor activity in diabetic gastroparesis, reflux in the upper digestive tract, and numerous other gastroenterological functional pathologies have also been observed.

In the treatment of obesity, electrical stimulation of the stomach delays the stomach transit by continuous disruption of the intrinsic electrical activity during periods of therapy. Such continuous disruption may result in weight loss by decreasing the cross sectional area of the stomach by inducing contractions, lessening the capacity of the stomach during periods of therapy, changing the intrinsic direction and frequency of the peristalsis during periods of therapy, and modulating the parasympathetic nervous system. Also in the treating obesity, electrical stimulation of the small intestine increases the small intestinal transit time by efficient electrical induction of peristalsis thereby reducing the level of absorbed components. In treatment of gastroparesis and other motility disorders, electrical stimulation improves gastric emptying by accelerating the transit time of food moving through the GI tract and/or relieving neurally mediated symptoms associated with gastroparesis. Thus, electrical stimulation increases frequency or amplitude of peristaltic contractions thereby intensifying the rapidity or force used to propel ingested components through the GI tract.

Recently, methods have been successfully employed whereby an electrical stimulation device is implanted on the stomach wall and/or small intestine. For example, U.S. Pat. No. 5,423,872 (Jun. 13, 1995) provided a process for the treatment of obesity and related disorder employing an electrical stimulator or pacemaker attached to the antrum or greater curvature of the stomach. U.S. Pat. No. 6,615,084 (Sep. 2, 2003) provided a process for the treatment of obesity and related disorder employing an electrical stimulator and pacemaker attached to the lesser curvature of the stomach. U.S. Pat. No. 5,690,691 (Nov. 25, 1997) provided a portable or implantable gastric pacemaker including multiple electrodes positionable on the inner or outer surface of an organ in the gastrointestinal tract which are individually programmed to deliver a phased electrical stimulation to pace peristaltic movement of material through the gastrointestinal tract. U.S. Pat. No. 6,606,523 (Aug. 12, 2003) provided an apparatus for stimulating neuromuscular tissue of the gastrointestinal tract and methods for installing the apparatus to the surface of the neuromuscular tissue. More recently, U.S. patent application Ser. No. 10/627,908 (filed Jul. 25, 2003) provides methods whereby an electrical stimulation device is implanted on the small intestines or lower bowel. All of the patents, patent applications, and publications cited in the present specification are incorporated by reference.

Typically, a lead conveys the electrical stimulation from the electrical stimulator to the gastrointestinal tissue. A known method for implanting such a lead into the gastrointestinal tissue is accomplished by inserting, typically through a trocar (rigid tube with airtight valves), a needle with a thread attached at one end and a lead attached at the other. Another approach utilizes a lead with a needle incorporated into one end, wherein the needle is implanted into the tissue and affixed by tines. However, both of the approaches above have the disadvantage that a tissue tunnel with a large diameter is created upon implantation of the device; such large diameter may allow movement of the electrodes. Such movement may be problematic when targeting particular areas of tissue for stimulation. Moreover, fibrosis and/or erosion, which may result for larger diameter tunnels, may cause a decrease in effectiveness of the therapy, a completely ineffective therapy, and/or tissue damage.

Gastrointestinal stimulation often requires high energy stimulation that is distributed over large electrode surface areas to avoid tissue damage. However, leads that are currently being used to convey electrical stimulation from the electrical stimulator to the gastrointestinal tissue are rigid. Rigid electrodes may be problematic because merely increasing the surface area of a rigid electrode increases the size of the electrode thus increasing the possibility of erosion. Also, rigid electrodes may decrease the compliance of the surrounding tissue and induce mechanical stress concentrations that may result in fatigue failures in the lead.

Therefore, it would be desirable to provide an implantable lead device which may be easily positioned and secured into the tissue. It would also be desirable to provide an implantable lead device which creates a smaller diameter in the tissue tunnel than prior devices, thereby lessening the likelihood that the electrodes will be displaced, especially where the tissue is undergoing repeated and/or vigorous movement. Further, it would be desirable to provide an implantable lead -device which utilizes flexible electrodes to facilitate compliance of the surrounding tissue and decrease the likelihood of mechanical stress concentrations that may result in fatigue failures in the lead.

SUMMARY OF THE INVENTION

An implantable lead device and method for implanting the lead, wherein the lead device electrically stimulates tissue within a patient's body and more particularly the lead device stimulates gastrointestinal tissue. The implantable lead may be inserted through the tissue with minimal expansion of the penetration tunnel and attached to the tissue being stimulated with minimal efforts or apparatus. The implantable lead has flexible properties thus minimizing the potential for electrode erosion, maximizing tissue compliance, and minimizing the mechanical stress concentration that may result in fatigue failure in the lead.

An implantable lead device for attachment to tissue to be stimulated within a patient's body, said device comprising: an elongated body having a proximal end and a distal end; an electric connection terminal at or near the proximal end for connection to a power source; at least one flexible electrode at or near the distal end; at least one electrical conductor extending through the elongated body from the flexible electrode to the electric connecter terminal whereby an electrical pathway may be formed between the flexible electrode, the electrical connection terminal, and the tissue to be stimulated; and a substantially flexible anchoring loop at or near the distal end, wherein the elongated body is narrow at or near the anchoring loop allowing the anchoring loop to be positioned for attachment within the patient's body.

An implantable lead device for attachment to tissue to be stimulated within a patient's body, said device comprising: an elongated body having a proximal end and a distal end; an electric connection terminal at or near the proximal end for connection to a power source; a penetration mechanism at the distal end to penetrate the tissue to be stimulated; a quick release connecting mechanism adjacent to the penetration mechanism to allow the penetration mechanism to be detached from the elongated body once the implanted device has been properly located within the tissue; at least one flexible electrode towards the distal end; at least one electrical conductor extending through the elongated body from the electric connection terminal to the flexible electrode, whereby an electrical pathway may be formed between the flexible electrode, the electrical connection terminal, and the tissue to be stimulated; and a substantially flexible anchoring loop at or near the distal end, wherein the elongated body narrows at or near the anchoring loop to allow the anchoring loop to be positioned for attachment with the patient's body.

A method for implanting a lead device for attachment to tissue to be stimulated within a patient's body, said method comprising: positioning an elongated body device with a distal end and a proximal end, wherein the elongated body has at least one flexible electrode at or near the distal end and an electric connection terminal at or near the proximal end for connection to a power source; forming an electrical pathway between the flexible electrode, the electrical connection terminal, and the tissue to be stimulated, wherein the electrical conductor extends through the elongated body from the electric connection terminal to the flexible electrode; and attaching a substantially flexible anchoring loop located at or near the distal end within the patient's body, wherein the elongated body is narrow at or near the anchoring loop.

A method for implanting a lead device for attachment to tissue to be stimulated within a patient's body, said method comprising: penetrating the tissue to be stimulated with a penetration mechanism; positioning an elongated body device with a distal end and a proximal end, wherein the elongated body has at least one flexible electrode at or near the distal end and an electric connection terminal at or near the proximal end for connection to a power source; forming an electrical pathway between the flexible electrode, the electrical connection terminal, and the tissue to be stimulated, wherein the electrical conductor extends through the elongated body from the electric connection terminal to the flexible electrode; detaching the penetration mechanism from the elongated body once the implant device has been properly located within the tissue, wherein a quick release connecting mechanism adjacent to the penetration mechanism allows the penetration mechanism to be detached; and attaching a substantially flexible anchoring loop located at or near the distal end within the patient's body, wherein the elongated body is narrow at or near the anchoring loop.

BRIEF DESCRIPTION OF THE DRAWINGS

FIG. 3 illustrates further embodiments wherein the implantable lead is implanted into the tissue to be stimulated. FIG. 3A illustrates the use of sutures or staples to attach the anchoring loop to the tissue. FIGS. 3B and 3C illustrate different embodiments wherein the proximal end of the flexible electrode is passed through the anchoring loop to lock the flexible electrode in place.

DETAILED DESCRIPTION OF THE PREFERRED EMBODIMENT

An implantable lead device and methods for implanting the lead, wherein the lead device electrically stimulates tissue within a patient's body and more particularly the lead device stimulates gastrointestinal tissue. The implantable lead may be inserted through the tissue with minimal expansion of the penetration tunnel and attached to the tissue being stimulated with minimal efforts or apparatus. The implantable lead has flexible properties thus minimizing the potential for electrode erosion, maximizing tissue compliance, and minimizing the mechanical stress concentration that may result in fatigue failure in the lead.

In order to further clarify the device and method of implantation of the device, FIGS. 1-4 are described. These device and method of implantation of the device, are especially suited for treating obesity and syndromes related to motor disorders of the stomach of a patient.

Figure 1A:
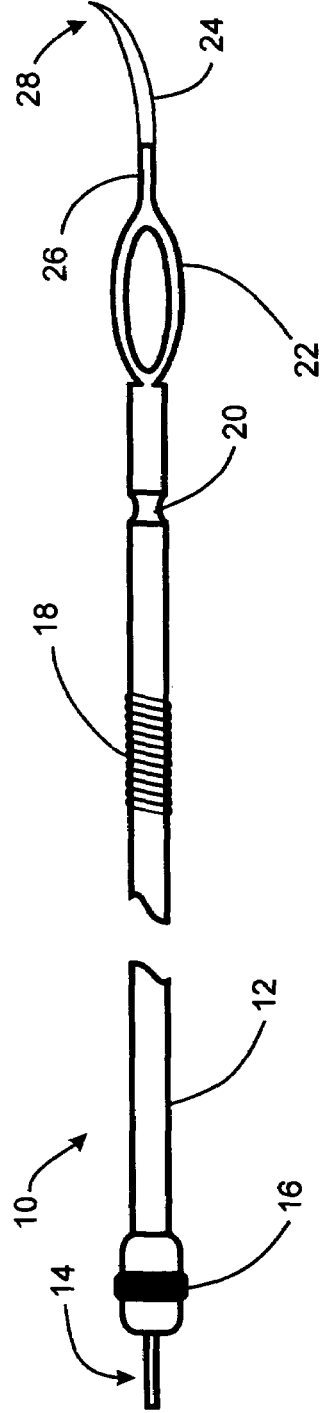
FIG. 1A illustrates an implantable lead having a flexible electrode for conveying electrical stimulation from the electrical stimulator to the tissue to be stimulated.

FIG. 1A illustrates an implantable lead 10 comprising an electrical connection terminal 16 located at the proximal end 14 of an elongated body 12, a flexible electrode 18 which may comprise one or more flexible electrode(s), a substantially flexible anchoring loop 22, a narrowing or "hinge" or "pivot point" 20 at or near the anchoring loop 22, and a penetrating mechanism 24 at the distal end 28. As shown in FIG. 1A, the narrowing 20 may be provided at a position between anchoring loop 22 and flexible electrode 18. Once the implantable lead is in place (i.e., in position adjacent or near the tissue to be stimulated), the penetrating mechanism is removable by cutting at position 26. The implantable lead 10 materials should be suitable for chronic implantation in the human body and have acceptable electrically conductive and insulative materials. The electrical connection terminal 16 is attached and/or inserted into an electrical power source (not shown). The electrical connection terminal 16 provides an electrical and/or mechanical interface to the electrical stimulator.

Figure 2A:
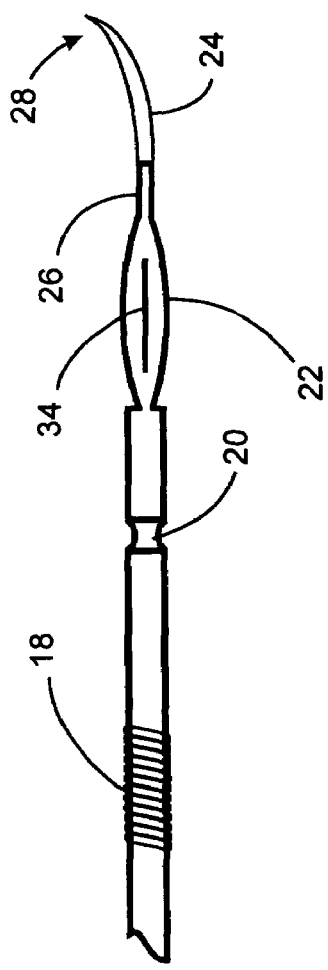
FIG. 2A illustrates a further embodiment wherein the anchoring loop is in the closed position due to tension placed along the length of the flexible electrode.
Figure 2B:
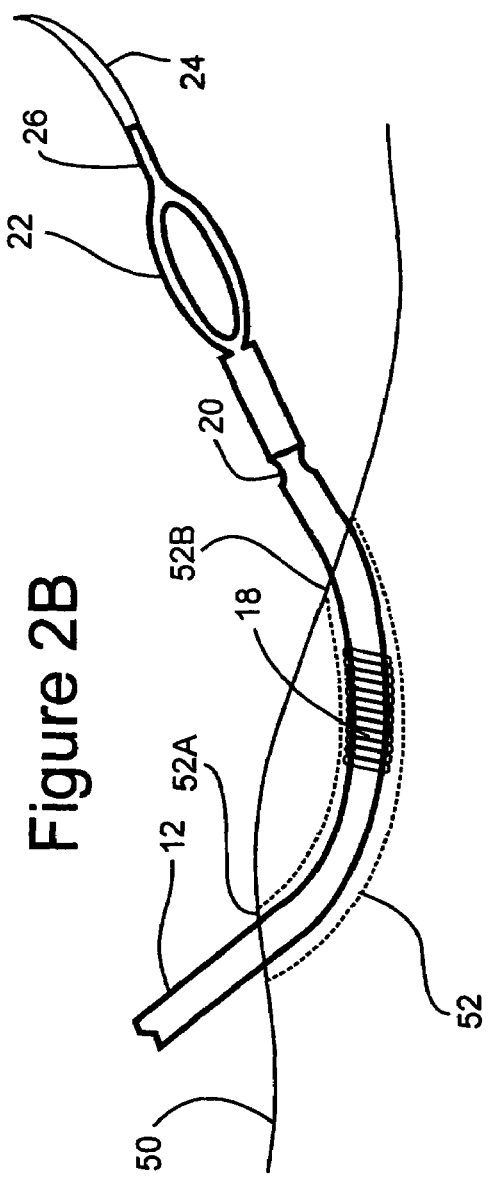
FIG. 2B illustrates the electrode placed within the tissue to be stimulated and the anchoring loop assuming its open position once the tension is removed.

As illustrated in FIG. 2, during implantation the penetrating mechanism 24 is passed through the tissue to be stimulated and the flexible electrode 18 is pulled through the penetration tunnel 52 (see FIG. 2B) created by the penetrating mechanism 24. In such cases, the distance from the distal end of the anchoring loop 22 to the distal end of the penetrating mechanism 24 is preferably greater than the internal distance through the penetration tunnel 52 so that end of the penetrating mechanism 24 can be grasped in order to pull the electrostimulation device through the penetration tunnel 52 and keep the electrostimulation device under tension. By keeping tension along the elongated body 12, the anchoring loop 22 is maintained in a "closed" position (see FIG. 2A with the normal opening or "hole" in the anchoring loop 22 collapsed to line 34). In this closed position, the anchoring loop 22 is collapsed to a diameter of approximately the same size as (or smaller than) the flexible electrode 18, so as not to enlarge the penetration tunnel 52 as it passes through. After the flexible electrode 18 is inserted into the penetration tunnel 52 and tension along the elongated body 12 is released, the anchoring loop 22 assumes its normal open position. In its normal open position, the anchoring loop 22 has a diameter that is larger than the diameter of the flexible electrode 18. The implantable lead 10 is then fixated by the anchoring loop 22 and the penetrating mechanism 24 is excised and removed from the body. The penetration mechanism 24 is detachable (e.g., by cutting at position 26) from the elongated body 12 once the implantable lead 10 has been properly located within the tissue to be stimulated.

The anchoring loop 22 preferably consists of substantially flexible, reinforced silicone elastomer or polymer which is normally in an open position (see FIG. 2B) but under tension is in a closed position (see FIG. 2A).

Figure 1B:
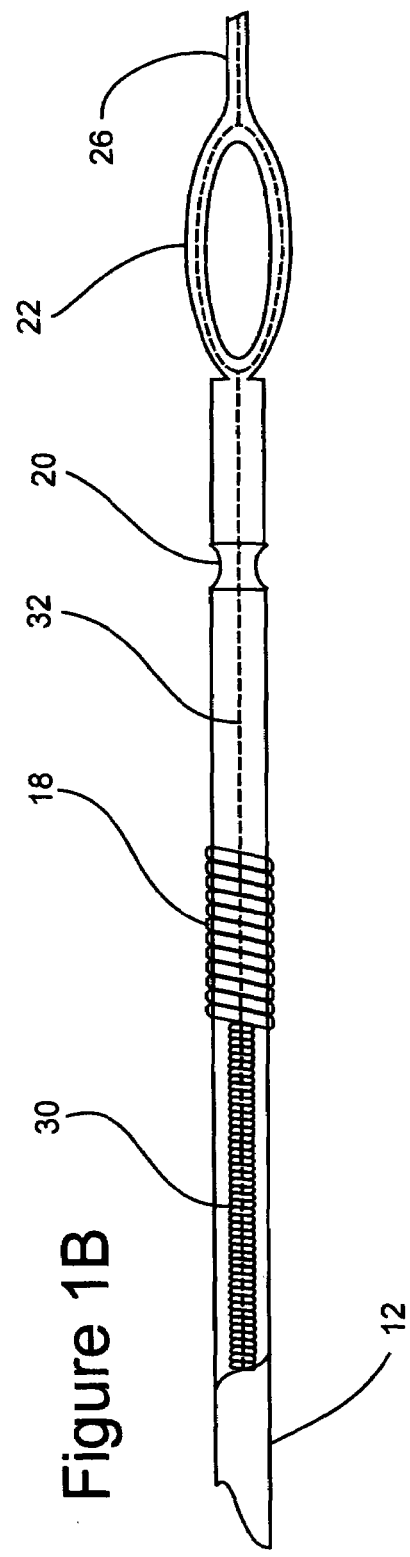
FIG. 1B further illustrates the flexible portion of the implantable lead.

FIG. 1B provides a more detailed view of the flexible portion of the implantable lead and shows the internal and flexible electrical conductor 30 leading from the electrical connection terminal 16 to the flexible electrode 18 as well as a strengthening element 32. The implantable lead 10 comprises a electrical connection terminal 16 located at the proximal end 14 of an elongated body 12, a flexible electrode 18, a narrowing or "hinge" or "pivot point" 20 at or near the anchoring loop 22, and a penetrating mechanism 24 at the distal end 28 which is detachable from the elongated body 12. Typically the elongated body 12 is comprised of the internal and flexible electrical conductor 30 insulated by an outer sheath (not shown) made of a silicone elastomer or polymer, or a like material. The electrical conductor 30 extends through the elongated body 12 from the flexible electrode 18 to the electrical connection terminal 16 at the proximal end 14. Thus, the flexible electrode 18 may be in communication with the electrical terminal connector 16 to form an electrical pathway between the flexible electrode 18, the electrical terminal connector 16, and the tissue to be stimulated. The flexible electrode 18 provides the electrical interface between the implantable lead 10 and the tissue to be stimulated. Preferably, the flexible electrode 18 is a conductive material configured as a helical coil of sufficient exposed surface area to conduct the anticipated energies from the implantable lead 10 to the tissue to be stimulated. Preferably, such a helical coil should include a means (e.g., a load bearing element) to prevent significant longitudinal stretching of the coil under tension while still allowing the desired flexibility. The flexible electrode 18 should exhibit good charge transference properties and low polarization potentials. An alternative embodiment of the flexible electrode 18 is a conductive helical coil which has been coated or impregnated with an electrically enhancing material to provide an optimum electrical connection between the implantable lead 10 and the tissue to be stimulated. A further alternative embodiment of the flexible electrode 18 is a flexible silicone or polymer base which is made conductive by coating or impregnation of a conductive material into the polymer or elastomer.

FIG. 2A and 2B illustrate the open and closed positions of the anchoring loop 22. In FIG. 2A, the anchoring loop 22 collapses under tension (generally applied only to the longitudinal axis of the elongated body 12) to create a small diameter profile when passing the implantable lead 10 through the penetration tunnel 52 (having entry 52A and exit 52B openings), thereby minimizing the stretching or enlargement of the penetration tunnel 52. Generally, the small diameter of the anchoring loop 22 in the closed position is the same as or less than the diameter of the flexible electrode 18. In FIG. 2B, the anchoring loop 22 assumes its more open or normal configuration when the anchoring loop 22 has passed through the penetration tunnel 52 (and tension has been removed from the elongated body 12).

FIG. 3 illustrates methods for attachment of the implantable lead to the tissue to be stimulated. In FIG. 3A, the anchoring loop 22 is sutured (see sutures 36) or stapled into the tissue to be stimulated in order to fixate the flexible electrode 18 within the tissue. Alternatively, a narrow strip of reinforced silicone elastomer or polymer which would allow sutures or staples to be placed through the strip and into the tissue to be stimulated could be used in place of the anchoring loop 22.

Figure 3C:
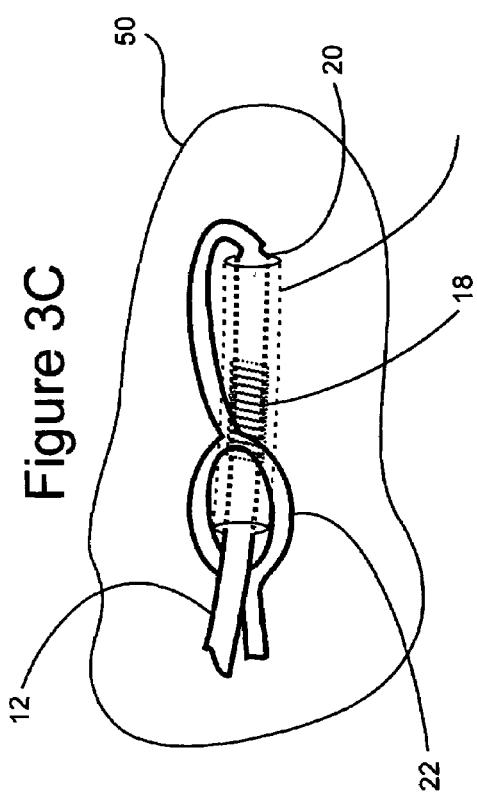

FIGS. 3B and 3C illustrate an additional attachment technique. In FIG. 3B the anchoring loop 22 assumes a more open position when the anchoring loop 22 has passed through the penetration tunnel 32 (and tension has been removed from the elongated body 12). The electrical connection terminal 16 is passed through the anchoring loop 22 in order to capture and/or ensnare the tissue to be stimulated. In FIG. 3C, the electrical connection terminal 16 is also passed through the anchoring loop 22 and the anchoring loop 22 is then folded back to lock the electrostimulation device in place. The narrowing, "hinge," or "pivot point" 20 at or near the anchoring loop 22 allows the anchoring loop 22 to be folded back and lie flat for attachment into the tissue to be stimulated. Additionally, the narrowing or "hinge" or "pivot point" 20, as shown in FIG. 3C, may prevent the elongated body 12 from tightening and constricting the ensnared tissue. Alternatively, a surgical clip may be applied at the "hinge" 20 to prevent tightening.

Figure 4B:
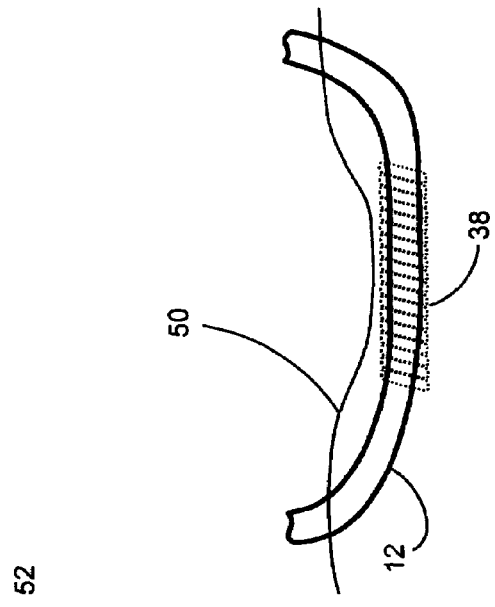
FIG. 4 compares the flexible electrode of this invention (FIG. 4A) and a prior art rigid electrode (FIG. 4B) when attached to the tissue to be stimulated The figures are not drawn to scale.
Figure 4A:
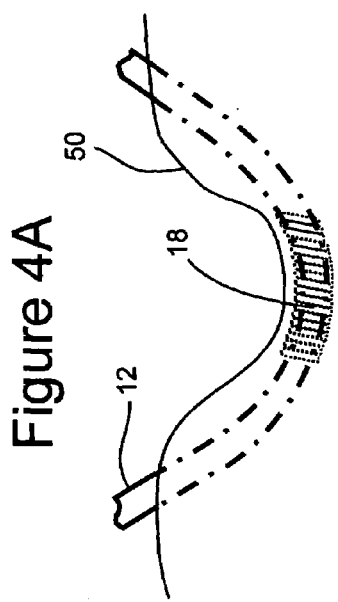

FIG. 4 compares a flexible electrode 18 of this invention with a rigid electrode 38 of the prior art. The natural configuration or shape of the tissue 50 to be stimulated is shown in FIG. 4A. Due to the flexible nature of the flexible electrode 18 of the present invention, the tissue through which the electrostimulation device passes is able to maintain its normal configuration or shape. In other words, the placement of the electrostimulation device and the penetration tunnel do not significantly distort the natural shape of the tissue. Moreover, the tissue is able to move in a more natural manner (e.g., during digestion or other bodily functions) due to the flexibility of the electrostimulation device. In contrast, the more rigid prior art electrode 38 effectively forces the penetration tunnel 52 (and the adjacent tissue) to adopt the shape and configuration of the rigid electrode 38; natural movement of the tissue will be, of course, significantly impaired. This can lead to tissue damage and/or impairment of stimulation. The rigid electrode 38 of the prior art forces the tissue movement to the ends of the rigid electrode 38 thereby preventing the normal flexing of the tissue. The rigid electrode 38 may also cause stress concentration of a sufficient magnitude to induce fatigue failure of the prior art electrostimulation device. Additionally, if the tissue is sufficiently muscular, the contraction may cause tissue irritation and/or tissue damage at the ends of the rigid electrode 38 where the tissue is pinched against the rigid electrode 38. Chronic tissue damage may result in fibrosis of the tissue surrounding the rigid electrode 38 or erosion of the rigid electrode 38 through the tissue.

The inventive flexible electrode 18 avoids these problems. As shown in FIG. 4A, the flexible electrode 18 more easily adopts the natural configuration and position of the tissue to be stimulated. Thus, the flexible electrode 18, especially for thin-walled tissue, minimizes the potential for electrode erosion, maximizes tissue compliance, and minimizes the mechanical stress concentration that may result in fatigue failure in the implantable lead 10. The flexible electrode 18 itself flexes and does not constrain the tissue to the extent of a rigid prior art electrode 38. Therefore, the irritation and stress concentrations are expected to be significantly less, and the potential for fatigue failure or erosion are expected to be significantly decreased.

The implantable lead is advantageous for conveying electrical stimulation to tissue (e.g., gastrointestinal tissue) without expansion of the penetration tunnel and attaching the implantable lead to the tissue being stimulated with minimal additional efforts or apparatus. Previous devices generally required a penetration tunnel with a larger diameter (due largely to the rigid nature of the electrode). After insertion, excessive movement of the electrode within such large diameter tunnels can result in fibrosis and/or erosion problems. Additionally, such large diameter tunnels make it more difficult to target particular areas or types of tissue (i.e., thin wall tissue or mechanically dynamic tissue) for stimulation.

Specifically for gastrointestinal tissue, using one or more flexible electrodes may be advantageous in reducing the adverse mechanical effects of electrical stimulation on the tissue being stimulated. Gastrointestinal stimulation typically requires high energy stimulation. Such high energy stimulation is generally applied using larger electrodes to prevent damage to the tissue. The properties of the flexible electrode of the present allow for the utilization of larger electrodes (relative to the prior art), thereby reducing the detrimental effects on the tissue to be stimulated.

As noted above, the electrostimulation device is to be connected to a power source. The power source may be implanted within the body or located external of the body. Preferably, the power source contains one or more batteries to provide the desired electrical energy to operate the electrostimulation device. More preferably, the batteries are of the rechargeable-type and, even more preferably, can be easily recharged without removing them from the body. The power source may also contain control mechanisms for the electrostimulation device. Such control mechanisms may include, for example, programable memory to monitor and/or control operating parameters (e.g., pulse amplitude, pulse rate, on-off cycling, and the like), communication circuits to allow health care workers to monitor the device and modify parameters, sensors (either within the power source or in communication with the power source) to detect, for example, food input in order to provide or withhold electrostimulation as appropriate, and the like.

Generally conventional laparoscopic or minimally invasive surgical techniques is used to place the desired electrical stimulation device or devices in the appropriate location(s) (e.g., on, or adjacent to, the stomach and small intestines, whereby electrical stimulation of the stomach and small intestines can be effected). Conventional electrical stimulation devices may easily be modified to include the flexible electrode described herein as well as the narrow point and anchoring loop. Such devices that could be modified include, for example, those described in U.S. Pat. No. 5,423,872 (Jun. 3, 1995) (an implantable gastric electrical stimulator at the antrum area of the stomach which generates sequential electrical pulses to stimulate the entire stomach, thereby artificially altering the natural gastric motility to prevent emptying or to slow down food transit through the stomach); U.S. Pat. No. 5,690,691 (Nov. 25, 1997) (a portable or implantable gastric pacemaker employing a number of electrodes along the greater curvature of the stomach for delivering phased electrical stimulation at different locations to accelerate or attenuate peristaltic movement in the GI tract); U.S. Pat. No. 5,836,994 (Nov. 17, 1998) (an implantable gastric stimulator which incorporates direct sensing of the intrinsic gastric electrical activity by one or more sensors of predetermined frequency bandwidth for application or cessation of stimulation based on the amount of sensed activity); U.S. Pat. No. 5,861,014 (Jan. 19, 1999) (an implantable gastric stimulator for sensing abnormal electrical activity of the gastrointestinal tract so as to provide electrical stimulation for a preset time period or for the duration of the abnormal electrical activity to treat gastric rhythm abnormalities); PCT Application Serial Number PCT/US98/10402 (filed May 21, 1998) and U.S. patent application Ser. No. 09/424,324 (filed Jan. 26, 2000) (implant device equipped with tines to help secure it in the appropriate location); U.S. Pat. No. 6,041,258 (Mar. 21, 2000) (electrical stimulation device with improved handle for laparoscopic surgery); U.S. patent application Ser. No. 09/640,201 (filed Aug. 16, 2000) (electrical stimulation device attachable to enteric or endo-abdominal tissue or viscera which is resistance to detachment); PCT Application Serial Number PCT/US00/09910 (filed Apr. 14, 2000;) entitled "Gastric Stimulator Apparatus and Method for Installing" based on U.S. Provisional Application Ser. Nos. 60/129,198 and 60/129,199 (both filed Apr. 14, 1999); PCT Application Ser. No. PCT/US00/10154 (filed Apr. 14, 2000;) entitled "Gastric Stimulator Apparatus and Method for Use" based on U.S. Provisional Application Ser. No. 60/129,209 (filed Apr. 14, 1999) and Ser. No. 60/466,387 (filed Dec. 17, 1999); and U.S. Provisional Patent Application Ser. No. 60/235,660 (filed Sep. 26, 2000) entitled "Method and Apparatus for Intentional Impairment of Gastric Motility and/or Efficiency by Triggered Electrical Stimulation of the Gastric Tract with Respect to the Intrinsic Gastric Electrical Activity." All of the patents, patent applications, provisional patent applications, and/or publications cited in the specification are hereby incorporated by reference.

The electrical stimulation devices preferably have a preset operating frequency and period which may obviously vary according to the alteration of stomach motility to be obtained and/or to the pathological condition of the patient. Generally, the gastric electrical stimulation device has an operating frequency of about 2 to about 15 pulses per minute. Preferably, the gastric electrical stimulation device employs stimulation of the stomach at a rate of about 2 to about 14 pulses/minute with each pulse lasting about 0.5 to about 4 seconds such that there is a pause of about 3 to about 30 between the pulses. More preferably, gastric electrical stimulation device employs the pulse rate is about 12 pulses/minute with each pulse lasting about 2 seconds with a pause of about 3 seconds between pulses. Preferably, the pulse amplitude is about 0.5 to about 15 milliamps. More preferable, each pulse: consists of a train of micro-bursts with a frequency of about 5 to about 100 $sec^{-1}$.

Preferably, the intestinal electrical stimulation device employs stimulation of the small intestines at a rate of about 2 to about 15 pulses/minute with each pulse lasting about 0.5 to about 4 seconds such that there is a pause of about 3 to about 30 seconds between the pulses. The electrical discharge of each pulse can vary from approximately 1 to 15 volts for voltage-controlled stimulation and from 2 to 15 milliamperes for constant current stimulation. More preferably, the pulse rate of the intestinal electrical stimulation device is about 12 pulses/minute with each pulse lasting about 2 seconds with a pause of about 3 seconds between pulses. Preferably, the pulse amplitude is about 0.5 to about 15 milliamps. More preferable, each pulse consists of a train of micro-bursts with a frequency of about 5 to about 100 $sec^{-1}$.

What is claimed is:

1. An implantable electrostimulation device for attachment to tissue to be stimulated within a patient's body, said-device comprising:
    an elongated body having a proximal end and a distal end;
    an electric connection terminal at or near the proximal end for connection to a power source;
    at least one flexible electrode at or near the distal end;
    at least one electrical conductor extending through the elongated body from the flexible electrode to the electrical connection terminal whereby an electrical pathway may be formed between the flexible electrode, the electrical connection terminal, and the tissue to be stimulated; and
    a substantially flexible anchoring loop at or near the distal end, the substantially flexible anchoring loop adapted to remain substantially flexible in substantially all configurations and positions,
    wherein the anchoring loon has a normal, open position in which the loop has a diameter that is larger than a diameter of the flexible electrode, and
    wherein the elongated body is narrow at a position between the flexible electrode and the anchoring loop to allow the anchoring loop to be positioned for attachment within the patient's body.

2. The device of claim 1, wherein the tissue to be stimulated is gastrointestinal tissue.

3. The device of claim 1, wherein the flexible electrode is configured as a helical coil.

4. The device of claim 3, wherein the helical coil has a sufficiently exposed surface area to provide an electrical interface between the device and the tissue to be stimulated.

5. The device of claim 3, wherein the helical coil does not significantly stretch along its longitudinal axis when placed under tension along its longitudinal axis.

6. The device of claim 3, wherein the helical coil has been coated or impregnated with a conductive material.

7. The device of claim 6, wherein the helical coil has a flexible silicone or polymer base that is coated or impregnated with the conductive material.

8. The device of claim 1, wherein the anchoring loop comprises a silicone elastomer or polymer loop.

9. The device of claim 1, wherein the anchoring loop is attached within the patient's body by sutures or staples.

10. The device of claim 1, wherein the anchoring loop has a closed position and the open position.

11. The device of claim 10, wherein the anchoring loop in the closed position has a diameter of about the same as or less than the flexible electrode's diameter.

12. The device of claim 10, wherein the flexible loop is configured to collapse from the open position to the closed position when tension is applied substantially along a longitudinal axis of the elongated body, and to assume the open position when the tension has been removed.

13. The device of claim 11, wherein the anchoring loop can be folded back to lie flat on the tissue.

14. The device of claim 11, wherein the proximal end of the elongated body can be passed through the anchoring loop to capture or surround the tissue.

15. The device of claim 1, wherein the narrowing between the flexible electrode and the anchoring loop prevents the anchoring loop from tightening or constricting the tissue.

16. The device of claim 1, wherein a surgical clip is applied at the narrowing between the flexible electrode and the anchoring loop to prevent the anchoring loop from tightening or constricting the tissue.

17. An implantable electrostimulation device for attachment to tissue to be stimulated within a patient's body, said device comprising:
    an elongated body having a proximal end and a distal end;
    an electrical connection terminal at or near the proximal end for connection to a power source;
    a penetration mechanism at the distal end to penetrate the tissue to be stimulated;
    a quick release connecting mechanism adjacent to the penetration mechanism to allow the penetration mechanism to be detached from the elongated body once the implanted device has been properly located within the tissue;
    at least one flexible electrode towards the distal end;
    at least one electrical conductor extending through the elongated body from the electrical connection terminal to the flexible electrode, whereby an electrical pathway may be formed between the flexible electrode, the electrical connection terminal, and the tissue to be stimulated; and
    a substantially flexible anchoring loop at or near the distal end, wherein the anchoring loop has a normal, open position in which the loop has a diameter that is larger than a diameter of the flexible electrode, and wherein the elongated body narrows between the flexible electrode and the anchoring loop to allow the anchoring loop to be positioned for attachment with the patient's body, the substantially flexible anchoring loop adapted to remain substantially flexible in substantially all configurations and positions.

18. The device of claim 17, wherein the tissue to be stimulated is gastrointestinal tissue.

19. The device of claim 18, wherein the flexible electrode is configured as a helical coil.

20. The device of claim 18, wherein the anchoring loop is attached within the patient's body by sutures or staples.

21. The device of claim 19, wherein the helical coil has a sufficiently exposed surface area to provide an electrical interface between the device and the tissue to be stimulated.

22. The device of claim 21, wherein the helical coil does not significantly stretch along its longitudinal axis when placed under tension along its longitudinal axis.

23. The device of claim 21, wherein the helical coil has been coated or impregnated with a conductive material.

24. The device of claim 23, wherein the helical coil has a flexible silicone or polymer base that is coated or impregnated with the conductive material.

25. The device of claim 17, wherein the flexible electrode is configured as a helical coil.

26. The device of claim 17, wherein the anchoring loop comprises a silicone elastomer or polymer loop.

27. The device of claim 17, wherein the anchoring loop has a closed position and the open position.

28. The device of claim 27, wherein the diameter of the anchoring loop in the closed position is less than or equal to the diameter of the flexible electrode.

29. The device of claim 27, wherein the anchoring loop assumes an open position when the anchoring loop is positioned for attachment within the patient's body.

30. The device of claim 27, wherein the flexible loop is configured to collapse from the open position to the closed position when tension is applied substantially along a longitudinal axis of the elongated body, and to assume the open position when the tension has been removed.

31. The device of claim 28, wherein the proximal end of the elongated body can be passed through the anchoring loop to capture or surround the tissue.

32. The device of claim 28, wherein the anchoring loop can be folded back to lie flat on the tissue.

33. The device of claim 17, wherein the narrowing between the flexible electrode and the anchoring loop allows the anchoring loop to be positioned on the tissue for anchoring into the tissue.

34. The device of claim 17, wherein the narrowing between the flexible electrode and the anchoring loop prevents the anchoring loop from tightening or constricting the tissue.

35. The device of claim 34, wherein a surgical clip is applied at the narrowing between the flexible electrode and the anchoring loop to prevent the anchoring loop from tightening or constricting the tissue.

36. A method for implanting an electrostimulation device for attachment to tissue to be stimulated within a patients body, said method comprising:
   forming a penetration tunnel within gastric tissue to be stimulated such that the penetration tunnel does not completely penetrate a wall of the stomach;
   positioning an elongated body device with a distal end and a proximal end in the penetration tunnel within the gastric tissue to be stimulated, wherein the elongated body has at least one flexible electrode at or near the distal end and the electrical connection terminal at or near the proximal end for connection to a power source;
   forming an electrical pathway between the flexible electrode, the electrical connection terminal, and the tissue to be stimulated, wherein the electrical conductor extends through the elongated body from the electric connection terminal to the flexible electrode; and
   attaching a substantially flexible anchoring loop located at or near the distal end within the patient's body, wherein the anchoring loop has a normal, open position in which the loop has a diameter that is larger than a diameter of the flexible electrode, and wherein the elongated body is narrow between the flexible electrode and the anchoring loop.

37. The method of claim 36, wherein the tissue to be stimulated is gastrointestinal tissue.

38. The method of claim 37, wherein the flexible electrode is configured as a helical coil.

39. The method of claim 38, wherein the helical coil has a sufficiently exposed surface area to provide an electrical interface between the device and the tissue to be stimulated.

40. The method of claim 38, wherein the helical coil has been coated or impregnated with a conductive material.

41. The method of claim 39, wherein the helical coil does not significantly stretch along its longitudinal axis when placed under tension along its longitudinal axis.

42. The method of claim 40, wherein the helical coil has a flexible silicone or polymer base that is coated or impregnated with the conductive material.

43. The method of claim 36, wherein the flexible electrode is configured as a helical coil.

44. The method of claim 36, wherein the anchoring loop comprises a silicone elastomer or polymer loop.

45. The method of claim 36, wherein the anchoring loop is attached within the patient's body by sutures or staples.

46. The method of claim 36, wherein the anchoring loop has a closed position and the open position.

47. The method of claim 46, wherein the diameter of the anchoring loop in the closed position is less than or equal to the diameter of the flexible electrode.

48. The method of claim 46, wherein the anchoring loop assumes an open position when the anchoring loop is positioned for attachment within the patient's body.

49. The method of claim 36, wherein the narrowing between the flexible electrode and the anchoring loop allows the anchoring loop to be positioned on the tissue for anchoring into the tissue.

50. The method of claim 49, wherein the anchoring loop can be folded back to lie flat on the tissue.

51. The method of claim 49, wherein the proximal end of the elongated body can be passed through the anchoring loop to capture or surround the tissue.

52. The method of claim 36, wherein the narrowing between the flexible electrode and the anchoring loop prevents the anchoring loop from tightening or constricting the tissue.

53. The method of claim 52, wherein a surgical clip is applied at the narrowing between the flexible electrode and the anchoring loop to prevent the anchoring loop from tightening or constricting the tissue.

54. The method of claim 36, wherein the flexible loop is configured to collapse from the open position to the closed position when tension is applied substantially along a longitudinal axis of the elongated body, and to assume the open position when the tension has been removed.

55. A method for implanting an electrostimulation device for attachment to tissue to be stimulated within a patient's body, said method comprising:
   providing an electrostimulation device having an elongated body with a distal end and a proximal end, wherein the elongated body has at least one flexible electrode at or near the distal end and an electrical connection terminal at or near the proximal end for connection to a power source;
   penetrating the tissue to be stimulated with the electrostimulation device using the penetration mechanism to form a penetration tunnel such that the penetration tunnel does not completely penetrate a wall of the stomach;
   positioning the electrostimulation device within the penetration tunnel of the tissue to be stimulated;
   forming an electrical pathway between the flexible electrode, the electrical connection terminal, and the tissue to be stimulated, wherein the electrical conductor extends through the elongated body from the electric connection terminal to the flexible electrode;
   detaching the penetration mechanism from the electrostimulation device once the electrostimulation device has been located within the tissue to be stimulated, wherein a quick release connecting mechanism adjacent to the penetration mechanism allows the penetration mechanism to be detached; and
   attaching a substantially flexible anchoring loop located at or near the distal end within the patient's body, wherein the anchoring loop has a normal, open position in which the loop has a diameter that is larger than a diameter of the flexible electrode, and wherein the elongated body is narrow between the flexible electrode and the anchoring loop.

56. The method of claim 55, wherein the tissue to be stimulated is gastrointestinal tissue.

57. The method of claim 55, wherein the flexible electrode is configured as a helical coil.

58. The method of claim 56, wherein the flexible electrode is configured as a helical coil.

59. The method of claim 58, wherein the helical coil has a sufficiently exposed surface area to provide an electrical interface between the device and the tissue to be stimulated.

60. The method of claim 59, wherein the helical coil does not significantly stretch along its longitudinal axis when placed under tension along its longitudinal axis.

61. The method of claim 58, wherein the helical coil has been coated or impregnated with a conductive material.

62. The method of claim 61, wherein the helical coil has a flexible silicone or polymer base that is coated or impregnated with the conductive material.

63. The method of claim 55, wherein the anchoring loop comprises a silicone elastomer or polymer loop.

64. The method of claim 55, wherein the anchoring loop is attached within the patient's body by sutures or staples.

65. The method of claim 55, wherein the anchoring loop has a closed position and the open position.

66. The method of claim 65, wherein the diameter of the anchoring loop in the closed position is less than or equal to the diameter of the flexible electrode.

67. The method of claim 65, wherein the anchoring loop assumes an open position when the anchoring loop is positioned for attachment within the patient's body.

68. The method of claim 55, wherein the narrowing between the flexible electrode and the anchoring loop allows the anchoring loop to be positioned on the tissue for anchoring into the tissue.

69. The method of claim 68, wherein the anchoring loop can be folded back to lie flat on the tissue.

70. The device of claim 68, wherein the proximal end of the elongated body can be passed through the anchoring loop to capture or surround the tissue.

71. The method of claim 55, wherein the narrowing between the flexible electrode and the anchoring loop prevents the anchoring loop from tightening or constricting the tissue.

72. The method of claim 71, wherein a surgical clip is applied at the narrowing between the flexible electrode and the anchoring loop to prevent the anchoring loop from tightening or constricting the tissue.

73. The method of claim 65, wherein the flexible loop is configured to collapse from the open position to the closed position when tension is applied substantially along a longitudinal axis of the elongated body, and to assume the open position when the tension has been removed.

* * * * *